United States Patent [19]

Ogi et al.

[11] Patent Number: 5,925,061
[45] Date of Patent: Jul. 20, 1999

[54] LOW PROFILE VASCULAR STENT

[75] Inventors: Darrell H. Ogi; Lilip Lau, both of Sunnyvale; Alan R. Klenk, Campbell, all of Calif.

[73] Assignee: Gore Enterprise Holdings, Inc., Newark, Del.

[21] Appl. No.: 08/782,114

[22] Filed: Jan. 13, 1997

[51] Int. Cl.⁶ .................................................. A61M 29/00
[52] U.S. Cl. .................................. 606/198; 623/1; 623/12
[58] Field of Search ............................... 606/1, 108, 191, 606/194, 195, 198, 200; 623/1, 12

[56] References Cited

U.S. PATENT DOCUMENTS

| | | |
|---|---|---|
| 3,152,618 | 10/1964 | Rothermel et al. . |
| 3,174,851 | 3/1965 | Buehur et al. . |
| 3,351,463 | 11/1967 | Rozner et al. . |
| 3,479,670 | 11/1969 | Medell . |
| 3,514,791 | 6/1970 | Sparks . |
| 3,562,820 | 2/1971 | Braun . |
| 3,625,198 | 12/1971 | Sparks . |
| 3,657,744 | 4/1972 | Ersek . |
| 3,710,777 | 1/1973 | Sparks . |
| 3,753,700 | 8/1973 | Harrison et al. . |
| 3,774,596 | 11/1973 | Cook . |
| 3,866,247 | 2/1975 | Sparks . |
| 3,866,609 | 2/1975 | Sparks . |
| 3,868,956 | 3/1975 | Alfidi et al. . |
| 3,927,422 | 12/1975 | Sawyer . |
| 3,949,073 | 4/1976 | Daniels et al. . |
| 3,953,566 | 4/1976 | Gore . |
| 3,974,526 | 8/1976 | Dardik et al. . |
| 4,130,904 | 12/1978 | Whalen . |

(List continued on next page.)

FOREIGN PATENT DOCUMENTS

| | | |
|---|---|---|
| 0 382 014 | 8/1990 | European Pat. Off. . |
| 0 408 245 | 1/1991 | European Pat. Off. . |
| 0 418 677 | 3/1991 | European Pat. Off. . |
| 0 472 731 | 3/1992 | European Pat. Off. . |
| 0 540 290 | 5/1993 | European Pat. Off. . |
| 0 556 850 | 8/1993 | European Pat. Off. . |
| 0 565 251 | 10/1993 | European Pat. Off. . |
| 0 686 379 | 12/1995 | European Pat. Off. . |
| 196 17 823 | 11/1997 | Germany . |
| 1 506 432 | 4/1978 | United Kingdom . |
| 1 567 122 | 5/1980 | United Kingdom . |
| 1 355 373 | 6/1994 | United Kingdom . |
| WO 88/06026 | 8/1988 | WIPO . |
| WO 90 04982 | 5/1990 | WIPO . |
| WO 92/06734 | 4/1992 | WIPO . |
| WO 92 09246 | 6/1992 | WIPO . |

(List continued on next page.)

OTHER PUBLICATIONS

Cragg, "Percutaneous Femoropopliteal Graft Placement" *Radiology* (1993)187 (3):643–648.

Hagen et al, "Self–Expandable Macroporous Nitinol Stents for Transfemoral Exclusion of Aortic Aneurysms in Dogs: Preliminary Results" *Cardiovascular Intervention Radiology* (1993) 16:339–342.

Cragg, et al.; Percutaneous Femoropopliteal Graft Placement; *Journal of Vascular and Interventional Radiology*; pp. 455–462; Jul.–Aug. 1993; vol. 4, No. 4.

Cragg et al.; Nitinol Intravascular Stent: Results of Preclinical Evaluation; *Radiology*; pp. 775–778; Dec. 1993; vol. 189, No. 3.

Laborde et al., "Intraluminal Bypass of Abdominal Aortic Aneurysm: Feasibility Study"; *Radiology* 1992, 184:185–190.

MinTec™ Minimally Invasive Technologies Product Brochure for the Craggstent and Cragg EndoPro System 1, 4 pages total.

Primary Examiner—Michael Buiz
Assistant Examiner—William Lewis
Attorney, Agent, or Firm—Morgan & Finnegan, LLP

[57] ABSTRACT

A low-profile, self-expanding vascular stent which is preferably cut from a thin tubing. The stent includes helical windings in a single helix, which are joined by bridges for longitudinal and radial strengthening.

22 Claims, 13 Drawing Sheets

U.S. PATENT DOCUMENTS

| | | |
|---|---|---|
| 4,164,045 | 8/1979 | Bokros et al. . |
| 4,187,390 | 2/1980 | Gore . |
| 4,319,363 | 3/1982 | Ketharanathan . |
| 4,411,655 | 10/1983 | Schreck . |
| 4,424,208 | 1/1984 | Wallace et al. . |
| 4,425,908 | 1/1984 | Simon . |
| 4,488,911 | 12/1984 | Luck et al. . |
| 4,494,531 | 1/1985 | Gianturco . |
| 4,503,569 | 3/1985 | Dotter . |
| 4,512,338 | 4/1985 | Balko et al. . |
| 4,546,500 | 10/1985 | Bell . |
| 4,553,545 | 11/1985 | Maass et al. . |
| 4,557,764 | 12/1985 | Chu . |
| 4,580,568 | 4/1986 | Gianturco . |
| 4,582,640 | 4/1986 | Smestad et al. . |
| 4,604,762 | 8/1986 | Robinson . |
| 4,629,458 | 12/1986 | Pinchuk . |
| 4,641,653 | 2/1987 | Rockey . |
| 4,642,117 | 2/1987 | Nguyen et al. . |
| 4,647,416 | 3/1987 | Seiler, Jr. et al. . |
| 4,649,922 | 3/1987 | Wiktor . |
| 4,655,771 | 4/1987 | Wallsten . |
| 4,665,906 | 5/1987 | Jervis . |
| 4,689,399 | 8/1987 | Chu . |
| 4,733,665 | 3/1988 | Palmaz . |
| 4,738,666 | 4/1988 | Fuqua . |
| 4,739,762 | 4/1988 | Palmaz . |
| 4,740,207 | 4/1988 | Kreamer . |
| 4,760,849 | 8/1988 | Kropf . |
| 4,776,337 | 10/1988 | Palmaz . |
| 4,787,899 | 11/1988 | Lazarus . |
| 4,798,606 | 1/1989 | Pinchuk . |
| 4,816,339 | 3/1989 | Tu et al. . |
| 4,820,298 | 4/1989 | Leveen et al. . |
| 4,830,003 | 5/1989 | Wolff et al. . |
| 4,842,575 | 6/1989 | Hoffman, Jr. et al. . |
| 4,856,516 | 8/1989 | Hillstead . |
| 4,878,906 | 11/1989 | Lindemann et al. . |
| 4,886,062 | 12/1989 | Wiktor . |
| 4,886,500 | 12/1989 | Lazarus . |
| 4,913,141 | 4/1990 | Hillstead . |
| 4,957,508 | 9/1990 | Kaneko et al. . |
| 4,969,458 | 11/1990 | Wiktor . |
| 4,990,151 | 2/1991 | Wallsten . |
| 4,990,155 | 2/1991 | Wilkoff . |
| 4,994,071 | 2/1991 | MacGregor . |
| 5,015,253 | 5/1991 | MacGregor . |
| 5,019,085 | 5/1991 | Hillstead . |
| 5,019,090 | 5/1991 | Pinchuk ................................. 606/194 |
| 5,035,706 | 7/1991 | Giantureo et al. . |
| 5,037,377 | 8/1991 | Alonso . |
| 5,037,427 | 8/1991 | Harada et al. . |
| 5,064,435 | 11/1991 | Porter . |
| 5,067,957 | 11/1991 | Jervis . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,122,154 | 6/1992 | Rhodes . |
| 5,123,917 | 6/1992 | Lee . |
| 5,133,732 | 7/1992 | Wiktor . |
| 5,139,480 | 8/1992 | Hickle et al. . |
| 5,147,370 | 9/1992 | McNamara et al. . |
| 5,151,105 | 9/1992 | Kwan-Gett . |
| 5,161,547 | 11/1992 | Tower . |
| 5,162,430 | 11/1992 | Rhee et al. . |
| 5,163,958 | 11/1992 | Pinchuk . |
| 5,171,262 | 12/1992 | MacGregor . |
| 5,192,307 | 3/1993 | Wall . |
| 5,195,984 | 3/1993 | Schatz . |
| 5,197,978 | 3/1993 | Hess . |
| 5,201,757 | 4/1993 | Heyn . |
| 5,209,735 | 5/1993 | Lazarus . |
| 5,211,658 | 5/1993 | Clouse . |
| 5,213,580 | 5/1993 | Slepian et al. . |
| 5,217,483 | 6/1993 | Tower . |
| 5,221,261 | 6/1993 | Termin et al. . |
| 5,236,447 | 8/1993 | Kubo et al. . |
| 5,242,451 | 9/1993 | Harada et al. . |
| 5,264,276 | 11/1993 | McGregor et al. . |
| 5,282,824 | 2/1994 | Gianturco . |
| 5,282,847 | 2/1994 | Trescony et al. . |
| 5,306,261 | 4/1994 | Alliger et al. . |
| 5,306,294 | 4/1994 | Winston et al. . |
| 5,314,472 | 5/1994 | Fontaine . |
| 5,324,304 | 6/1994 | Rasmussen . |
| 5,342,348 | 8/1994 | Kaplan . |
| 5,344,426 | 9/1994 | Lau et al. . |
| 5,354,308 | 10/1994 | Simon et al. . |
| 5,354,309 | 10/1994 | Schnepp-Pesch et al. . |
| 5,356,423 | 10/1994 | Tihon et al. . |
| 5,360,443 | 11/1994 | Barone et al. . |
| 5,366,473 | 11/1994 | Winston et al. . |
| 5,372,600 | 12/1994 | Beyar . |
| 5,382,261 | 1/1995 | Palmaz . |
| 5,405,377 | 4/1995 | Cragg . |
| 5,405,378 | 4/1995 | Strecker . |
| 5,421,955 | 6/1995 | Lau et al. . |
| 5,423,849 | 6/1995 | Eugelson et al. . |
| 5,443,500 | 8/1995 | Sigwart . |
| 5,449,373 | 9/1995 | Pinchasik et al. . |
| 5,458,605 | 10/1995 | Klemm . |
| 5,480,423 | 1/1996 | Ravenscroft et al. . |
| 5,484,444 | 1/1996 | Braudschweiler . |
| 5,496,365 | 3/1996 | Sgro . |
| 5,507,767 | 4/1996 | Maeda et al. ........................... 606/198 |
| 5,509,902 | 4/1996 | Raulerson . |
| 5,514,154 | 5/1996 | Lau et al. . |
| 5,522,881 | 6/1996 | Lentz . |
| 5,540,701 | 7/1996 | Sharkey et al. . |
| 5,540,712 | 7/1996 | Kleshinski et al. . |
| 5,545,210 | 8/1996 | Hess et al. . |
| 5,549,635 | 8/1996 | Solar . |
| 5,549,663 | 8/1996 | Cottone, Jr. ................................ 623/1 |
| 5,554,180 | 9/1996 | Turk . |
| 5,556,413 | 9/1996 | Lam . |
| 5,562,726 | 10/1996 | Chuter . |
| 5,571,173 | 11/1996 | Parodi . |
| 5,575,816 | 11/1996 | Rudnick et al. . |
| 5,591,197 | 1/1997 | Orth et al. . |
| 5,607,442 | 3/1997 | Fischell et al. ......................... 606/198 |
| 5,662,713 | 9/1997 | Andersen et al. . |

FOREIGN PATENT DOCUMENTS

| | | |
|---|---|---|
| WO 93 13825 | 7/1993 | WIPO . |
| WO 93/19803 | 10/1993 | WIPO . |
| WO 93/19804 | 10/1993 | WIPO . |
| WO 93/22986 | 11/1993 | WIPO . |
| WO 94/00179 | 1/1994 | WIPO . |
| WO 94/01483 | 1/1994 | WIPO . |
| WO 94/04097 | 3/1994 | WIPO . |
| WO 94/12136 | 6/1994 | WIPO . |
| WO 94/15549 | 7/1994 | WIPO . |
| WO 95/05132 | 2/1995 | WIPO . |
| WO 95/26695 | 10/1995 | WIPO . |

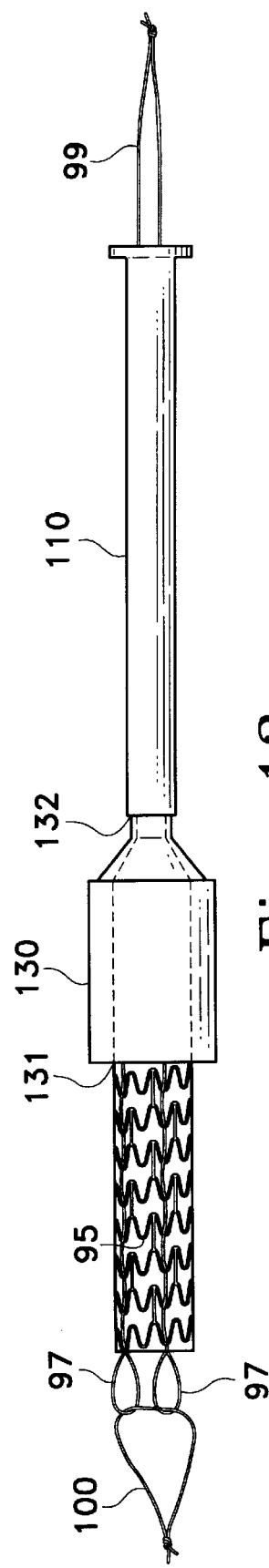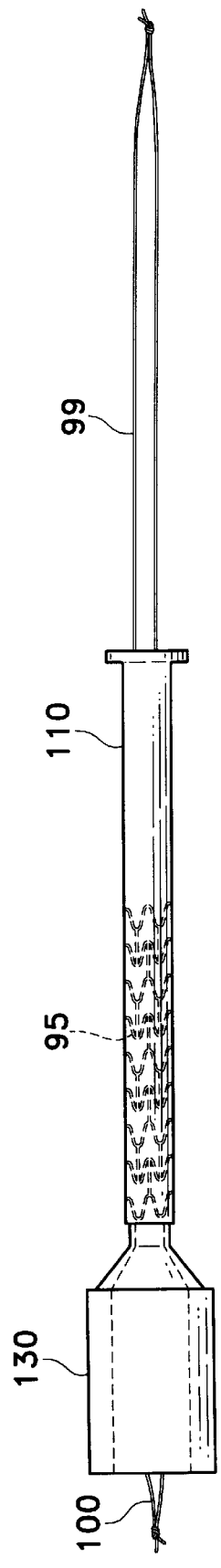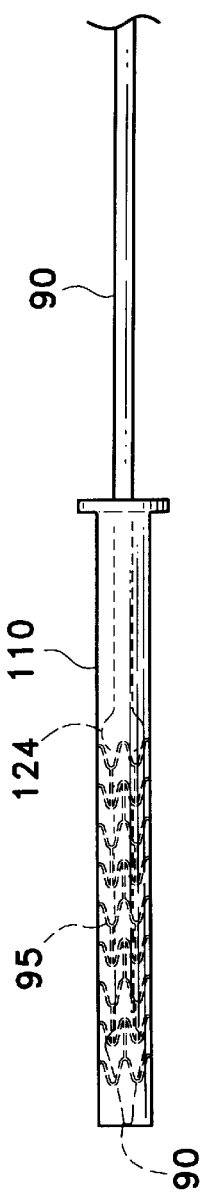

LOW PROFILE VASCULAR STENT

FIELD OF THE INVENTION

The present invention relates generally to implants for the treatment of bodily vasculature, ducts and the like. More specifically, the invention relates to low profile, vascular stents which are particularly useful for small diameter vascular applications.

BACKGROUND OF THE INVENTION

One method of treatment of diseased or otherwise damaged vasculature has traditionally been through the implantation of vascular stents and/or grafts to maintain patency of the vasculature. It has also been known to implant such devices in saphenous vein bypass grafts, either at the time of bypassing the coronary arteries, or at a later date when the saphenous vein graft becomes partially or totally occluded.

Although wire stents are generally acceptable for use in larger vessels, because of the generally reduced cross-sectional area available for blood flow in smaller vessels, the use of a wire stent often encroaches to an unacceptable extent within the lumen of the vessel, causing blood cell damage and possibly clotting. Similarly, stents which are formed of two or more overlapping helices present an encroachment problem into the lumens of smaller vessels, such as the carotid artery, coronary artery, etc. An additional problem with grafts fashioned from wire, is that it is difficult to reduce (e.g., through folding, radial compression or other reduction technique) the downsized versions to an acceptable profile for insertion through and placement in the smaller sized vessels.

Stents which are formed of a series of interconnected rings, with the rings being substantially perpendicular to the longitudinal axis of the stent are also known. Because of variations in the cross-sectional mass of this type of stent along the longitudinal axis, this type of stent will tend to buckle in the weakest locations, e.g., generally in the locations where the rings are interconnected.

Many varieties of stents and stent-grafts have been described, but include one or more of the drawbacks discussed above. Pinchuk, U.S. Pat. No. 5,163,958, discloses a helically wrapped, undulating wire stent coated with a layer of pyrolytic carbon. The wire stent includes a plurality of generally circumferential sections 22, which are formed from the same continuous, substantially helically wrapped, undulating length.

Lau et al., U.S. Pat. No. 5,421,955, discloses an expandable stent made of a plurality of radially expandable cylindrical elements interconnected by one or more interconnective elements. The cylindrical elements may be individually formed from undulating elements. The entire stent may be made from a single length of tubing.

Schnepp-Pesch et al., U.S. Pat. No. 5,354,309, discloses a stent including a memory alloy part which radially widens at a transition temperature that is above ambient temperature but below body temperature. The stent may include a helically wound wire, as shown in FIGS. 4a–4b.

Leveen et al., U.S. Pat. No. 4,820,298, discloses a flexible stent constructed of a helix made from medical thermoplastic. Adjacent loops of the helix are interconnected by elastomeric strands. This allows the stent to be stretched into a somewhat extended, linear configuration, and to resume its helical shape upon release of the stretching forces.

Lau et al., U.S. Pat. No. 5,514,154, discloses an expandable stent made of a plurality of individual radially expandable cylindrical elements interconnected by one or more interconnective elements. The cylindrical elements may be individually formed from undulating elements. The entire stent may be made from a single length of tubing. The cylindrical elements include radially outwardly extending anchoring projections which may increase the profile of the expanded stent.

In summary, various stents, such as those discussed above, have been described with varying degrees of success. What has been needed and is addressed by the present invention, is a stent which has a high degree of flexibility for advancement through torturous pathways of relatively small diameter, can be readily expanded, and has sufficient mechanical strength to maintain patency of the lumen into which it is implanted, while minimizing the amount of lumenal encroachment to reduce the thrombosis risk.

SUMMARY OF THE INVENTION

The present invention involves an expandable stent which is relatively flexible along its longitudinal axis, while at the same time being provided with structures to increase the columnar strength thereof.

According to an embodiment of the present invention, a self-expanding stent includes a structure having helical windings forming a generally tubular shape, and bridges interconnecting the helical windings. Preferably, the bridges are helically arranged within the structure. Preferably, the stent is self-expanding. However, the embodiments are also included within the invention, including balloon-expandable stents.

The stent according to the present invention may be formed from a thin-walled tubing, Preferably the stent is cut from the tubing by laser cutting or by EDM (i.e., Electrical Discharge Machining), techniques which are known in the art.. However, various etching techniques may also be used. The thin-walled tubing also contributes to the low profile of the stent..

The bridges may be circumferentially and substantially equiangularly located about the helix, with respect to one another. Preferably, the bridges are located at an interval of about 2 to 4 bridges per 360° of helical winding. More preferably, the bridges are located at an interval of about 3 bridges per 360° of helical winding.

The bridges may be formed as substantially straight bridges. Alternatively, at least one of the bridges (and as many as all of the bridges) may include or act as a spring having a predetermined spring constant. The spring(s) may be formed as an undulating spring. Alternatively, the spring (s) may be formed as a leaf-spring or other equivalent spring mechanism providing a comparable spring constant.

Preferably, at least one spring is aligned in a direction substantially parallel to the longitudinal axis of the generally tubular shape.

The helical windings of the helical structure and the bridges may have substantially equal widths. Alternatively, the widths of one or more of the bridges may be varied to alter the flexibility of the stent. Preferably, alterations are done to reduce the widths of the bridges with respect to the width of the helical windings of the helical structure, so as to increase the flexibility of the stent.

Preferably, the windings of the helical structure undulate in a direction substantially parallel to the longitudinal axis of the generally tubular shape. The low profile, self-expanding stent of the present invention preferably includes a single helical structure having windings forming a generally tubular shape having a longitudinal axis, and the single helical structure is formed from a thin-walled tubing. Also, the stent preferably includes bridges interconnecting the windings of the helical structure, and undulations in the windings. The undulations enhance the expandability of the stent. Additionally, the bridges may be aligned in a direction substantially parallel to the longitudinal axis of the generally tubular shape.

Preferably, the bridges are circumferentially and substantially equiangularly located about the helix, with respect to adjacent ones of the bridges.

The bridges may be helically arranged in the structure. Preferably, the bridges are positioned to form a ratio of about 3 bridges per 360° of windings.

The stent may further include asymmetrical undulations in at least one of the helical windings, to compensate for uneven expansion which occurs due to the helical nature of the stent.

Other features and advantages of the present invention will become more apparent from the following detailed description of the invention, when read in view of the accompanying exemplary drawings.

BRIEF DESCRIPTION OF THE DRAWINGS

FIGS. 13a, 13b, 13c, 13d, 13e and 13f show various stages of preparation for deployment, and deployment of, a stent according to the present invention.

DETAILED DESCRIPTION OF THE PREFERRED EMBODIMENTS

Figure 1:
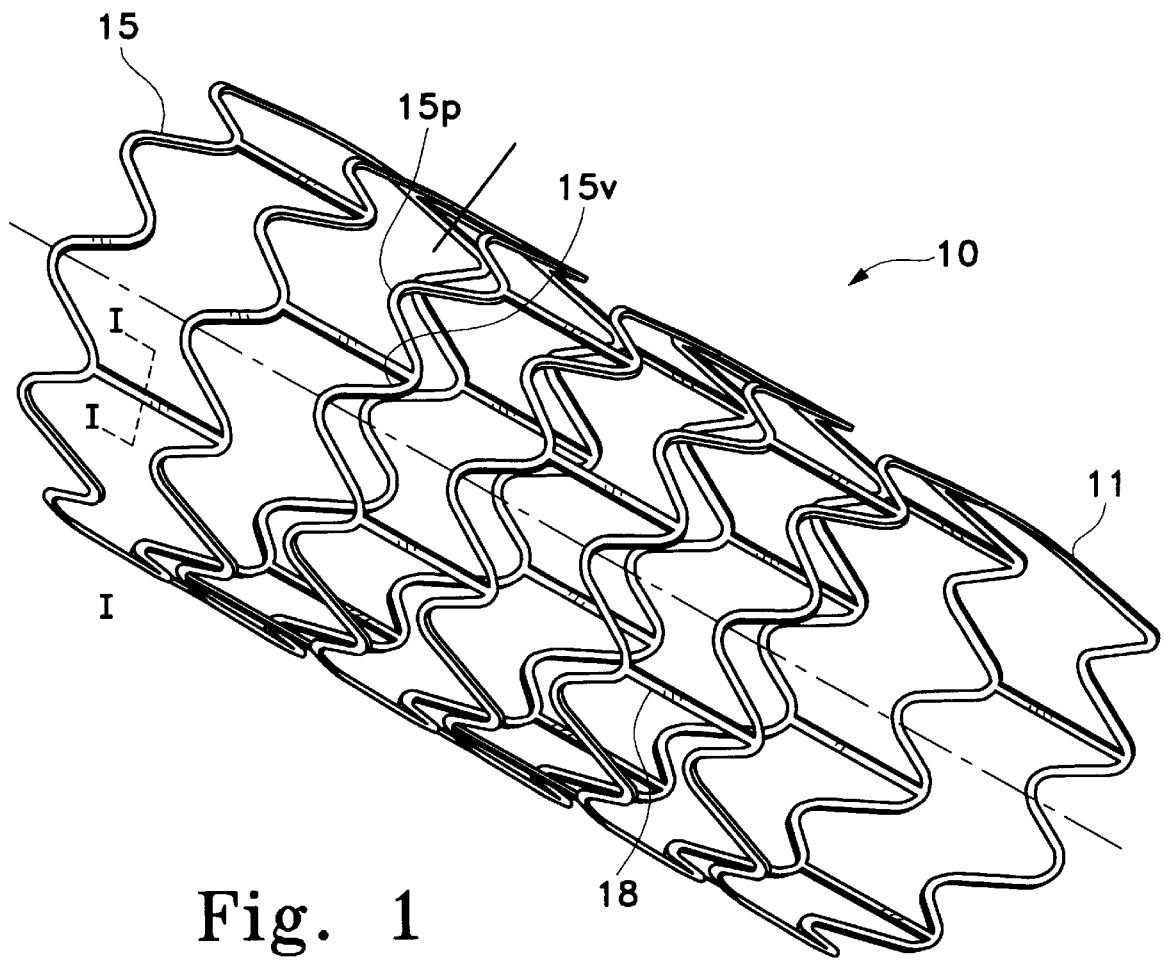
FIG. 1 is a perspective view of a first embodiment of a stent embodying features of the present invention.

FIG. 1 illustrates a self-expanding stent constructed according to principles of the present invention. For use in relatively small diameter vessels, (e.g., carotid artery, coronary artery, saphenous vein graft), a simple downsizing of available stents which have been used for larger vessels has been generally unsatisfactory for use in implantation. For example, when a known design using nitinol wire and expanded polytetrafluoroethylene was reduced in size (particularly in the diameter dimension), the radial stiffness decreased below an acceptable lower limit.

The flexibility of the stent facilitates delivery of the stent through torturous body lumens, including, but not limited to coronary arteries, carotid arteries and saphenous vein grafts, where, in addition to being torturous, the vessel diameters are small.

In FIG. 1, self-expanding stent 10 generally comprises a continuous mesh pattern of sinusoidal or undulating member 15 formed into a helical pattern of helical windings to form substantially cylindrical, tube-shaped structure 11. The undulating member undulates to form bends 15p and 15v which are generally oppositely oriented in the direction of the longitudinal axis of cylindrical structure 11. The helical windings formed by the undulating member are joined by bridges 18 to provide the stent with columnar strength and radial strength, and also stability to minimize changes in the length of the stent upon expansion thereof. Bridges 18 also provide improved kink resistance upon bending of the stent 10, and resist bowing of the stent when implanted to bridge an aneurysm, for example. Helical stents which lack bridges are more susceptible to columnar compression and buckling. This problem is particularly noted in the treatment of aneurysms, where the stent or stent-graft is positioned to span the enlarged section forming the aneurysm. A stent without bridges often buckles due to the forces applied by the blood flow through the upstream end of the stent, which tend to act locally against the column strength of that end. The result is buckling of the central portion of the stent or stent-graft, such that the stent or stent-graft follows the contour of the aneurysm. Ultimately, the upstream end of the stent or stent-graft can be pulled out of the aneurysmal neck and into the aneurysmal sac, thereby allowing the blood flow to bypass the stent or stent-graft altogether. This results in total failure in the case of a stent-graft, since hydraulic isolation of the aneurysmal sac has been lost at this point.

Bridges 18 increase the axial stiffness and columnar strength of stent 10, as noted above. The forces applied by the blood flow through the upstream end of stent 10 are axially distributed along the stent 10 through the bridges 18. Thus, even when the stent 10 spans an aneurysm, some of the force of the blood flow through stent 10 will be transferred to the distal end of stent 10, on the opposite end of the aneurysm. Since the distal (downstream) end will also be at least in frictional contact with the vessel into which the stent is implanted, opposing forces to the blood flow can be generated at both the upstream and downstream ends of stent 10. This decreases the overall tendency to push the upstream end down along the vessel pathway and further reduces the tendency of the graft to move into the site of the aneurysm and follow the path of the expanded vessel. Even if some buckling does occur, the bridges 18, having a tendency to keep the axial spacing of the helical turns at a constant, act as springs in this situation, storing energy which then acts to restore the stent to an unbuckled state. Stents without bridges have a much reduced ability in this regard.

Figure 3:
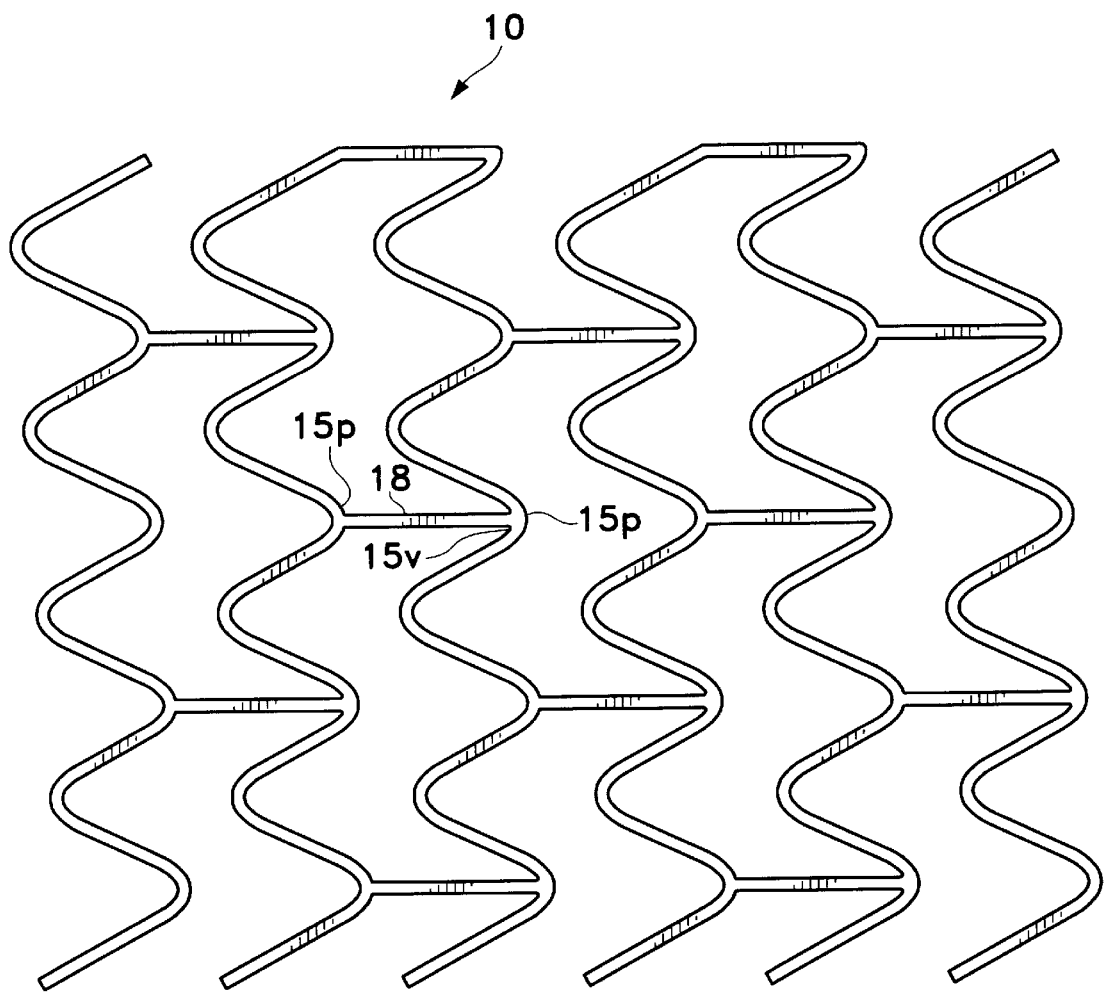
FIG. 3 is a plan view of a flattened section of a stent according to the first embodiment, which illustrates the interrelationship between the undulating, helical pattern and the interconnecting bridges of the stent shown in FIG. 1.

The number of bridges 18 in a stent should be kept to an acceptable minimum to enable the profile of the stent to be minimized during delivery. Preferably, bridge configurations forming a ratio of about two to four bridges per helical turn (i.e., 360°) are believed to be acceptable, with the preferred configuration being a ratio of about three bridges per helical turn as shown in FIG. 3, for example. The bridge configuration of three bridges per helical turn provides an offset arrangement of the bridges between adjacent windings or turns. Such an arrangement maintains the axial bending flexibility of the stent in virtually all directions, which is important for placement through torturous pathways.

Figure 4:
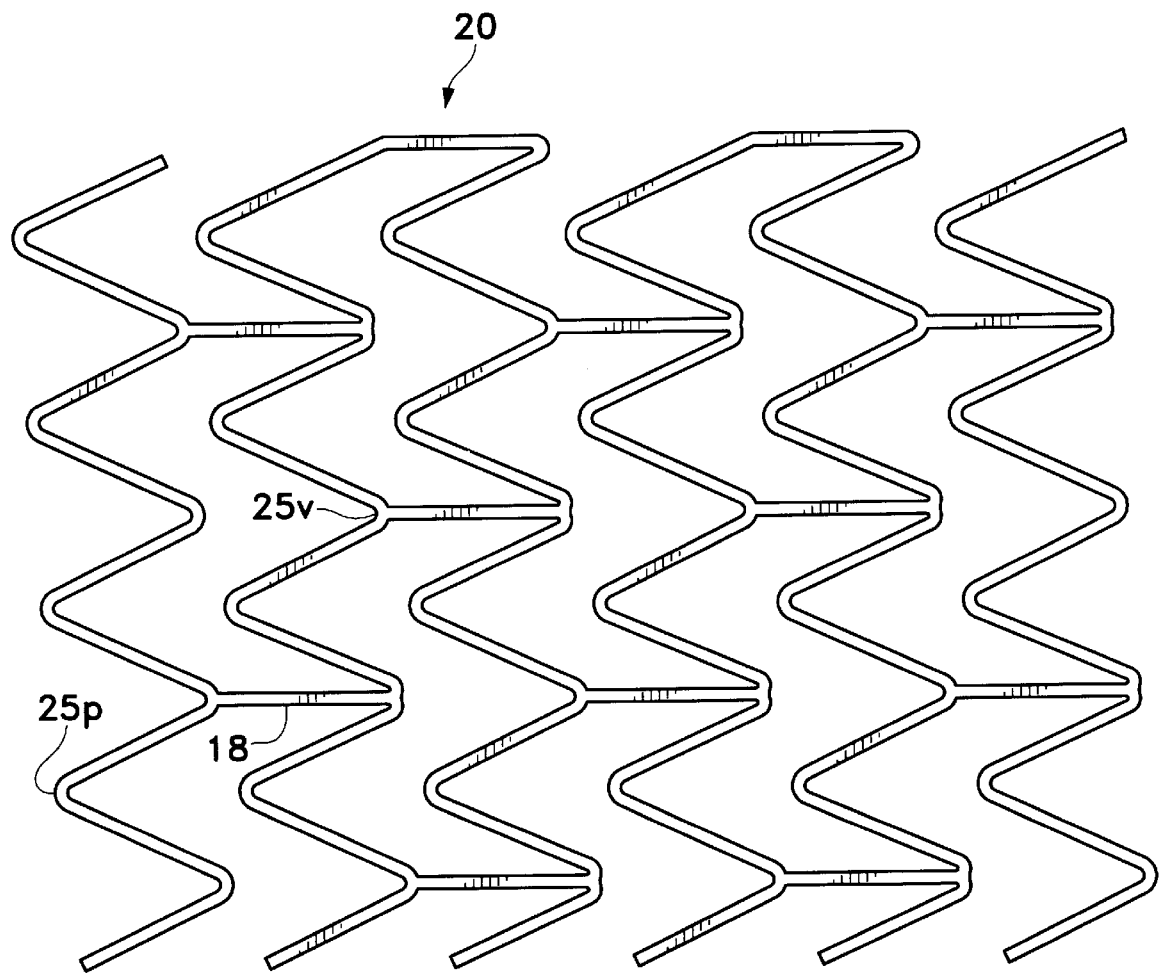
FIG. 4 is a plan view of a flattened section of a stent according to a second embodiment, which illustrates the interrelationship between the undulating, helical pattern and the interconnecting bridges of the second embodiment.

The bridges 18 are preferably interconnected between adjacent bends 15p and 15v of the undulating helical turns in order to prevent shortening of the stent during the expansion thereof, see FIGS. 3 and 4. It is noted however, that such a configuration is not absolutely necessary for length maintenance of the stent during expansion, and that the length can be substantially maintained as long as the bridges 18 are interconnected between the same corresponding locations on adjacent windings throughout the stent. For example, the bridges could be interconnected between adjacent windings midway between bends on each adjacent winding, with consistent corresponding placement of the remaining bridges. It is further noted that although winding is preferred to provide adjacent bends 15p and 15v (i.e., "in-phase" winding), other winding configurations are also possible. For example, helical windings may be arranged so that bridges longitudinally align with and connect adjacent bends 15p and 15p ("out-of-phase" winding). Other winding arrangements are also possible.

Preferably, the entire structure of the stent is formed from a thin-walled tube. This construction minimizes the wall thickness and lumenal encroachment of the stent, within the lumen of the vessel into which the stent is placed. At the same time, radial and longitudinal strength are maintained, without sacrificing flexibility or delivery profile. This minimizes the risks of blood cell damage and thrombosis associated with disruption of the blood flow profile.

The stent may be made by many different methods, including known chemical etching techniques and preferably, by laser cutting (e.g., Nd:Yag) from the tubing. Another preferred method of making stents according to the present invention is by Electric Discharge Machining (i.e., EDM), a technique known in the art. A preferred method of etching includes coating a thin-walled tubular member, such as nickel-titanium tubing, with a material which is resistive to chemical etchants, and then removing portions of the coating to expose the underlying tubing which is to be removed, but leaving coated portions of the tubing in the desired pattern for the stent so that subsequent etching will remove the exposed portions of the metallic tubing, but will leave the portions of the tubing which are to form the stent relatively untouched. The etchant-resistive material may then be removed from the stent by means of a machine-controlled laser according to known methods.

Preferably the stent undergoes a finishing process of electrochemical polishing by any of a number of techniques known in the art. Although such polishing reduces the overall dimensions of the members of the stent, and thereby weakens the stent with regard to its pre-polishing characteristics, this effect is overcome by simply "designing in" the additional dimensions of the material to be removed by electrochemical polishing, so as to end up with a stent having the desired dimensions and strength characteristics. Advantages obtained from the electrochemical polishing are that a smoother surface results, thereby reducing thrombosis, reducing the resistance to blood flow, making the stent more biocompatible. Electrochemical polishing also enhances the fatigue resistance of the stent and reduces the risk of balloon rupture in cases of stents which are not self-expandable but require expansion using a balloon catheter. Additionally, a smoother surface enables a lower friction with a funnel which is used to compress the stent, as discussed below, thereby rendering compression of the stent easier.

The tubing may be made of suitable biocompatible material such as stainless steel, titanium, tantalum, Elgiloy( a Co—Cr alloy), superelastic NiTi alloys (e.g., "nitinol"), and high strength thermoplastic polymers. The preferred materials are NiTi alloys and particularly "binary nitinol" (i.e., 50% Ni and 50% Ti by weight).

The desired pattern can be cut from a tubing having already been expanded and heat set according to known methods, or it can also be cut from a smaller diameter tubing, and then expanded and heat set at a larger diameter. When the stent is made of nitinol, the afore-described heat setting steps are included. However, as noted above, the stent may also be prepared from materials such as stainless steel (e.g. 316 L stainless) and other materials which do not form a self-expandable stent but must be expanded by other methods such as expansion by a balloon catheter. In these examples, the heat set step is unnecessary and is not performed.

Figure 2:
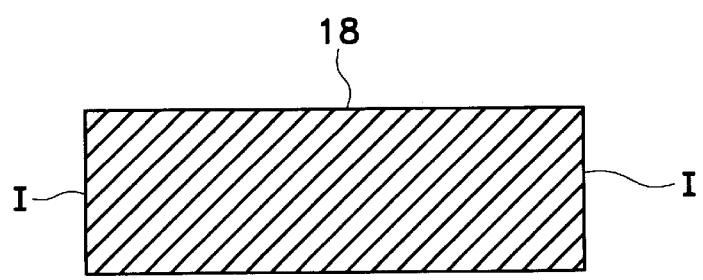
FIG. 2 is a cross-sectional view of a bridge taken along line I—I in FIG. 1.

As shown in FIG. 2, the cross-sectional configuration of the bridges 18, as well as the undulating member 15 which has the same cross-section in this embodiment, is rectangular. This configuration provides greater radial rigidity for a given wall thickness, compared to the circular cross-section which is provided by a wire stent. Consequently, for a given radial strength, the stent formed from a thin radial tubing according to the present invention can be formed significantly thinner than a stent formed from wire, thereby affording a lower intralumenal profile and less impedance of blood flow, in addition to the other advantages discussed above. It is noted that the thicknesses of the undulating member and bridges are substantially equal to each other in all embodiments of the instant invention, although the comparative widths of the same may vary.

The greater radial rigidity, discussed above, also allows the stent to be formed as a single helical structure, which greatly reduces the intralumenal profile. The stent has no anchoring projections in its expanded configuration, which further contributes to the low profile of the stent. The bridges make the stent longitudinally stiffer than a helical structure which lacks bridges, and also ensure that there is significantly less length change of the stent upon expansion of the same.

Additionally, the strength, flexibility and expandability of the present invention eliminate the need for secondary attachment methods, such as sutures, which also add thickness and thereby increase the lumenal encroachment and roughen the lumenal surface to increase the disruption of the blood flow profile, or may adversely affect the delivery profile of a stent.

Further, it is believed that the helical stent according to the present invention can be compressed to a smaller delivery profile than can a stent formed of individual rings, or other ring type structure, as discussed below with regard to FIGS.

10 and 11, and certainly smaller than a wire or double helix type configuration.

Additionally, the helix configuration according to the present invention has been found to be more flexible, particularly in the axial or longitudinal direction, than ring type stents. Still further, the rings in a ring type stent are independently expandable, which may lead to discontinuities in the expansion profile. In contrast, the helical stent according to the present invention is continuously expandable and therefor does not run the risk of forming discontinuities or "steps" upon expansion of the device, thereby resulting in a smoother lumen. This results in better hemodynamics through the stent when implanted, thereby reducing the risk of thrombosis.

FIG. 4 shows a plan view of a flattened section of a second embodiment of a stent according to the present invention. In this embodiment the bends 25p and 25v are notably sharper than those of the first embodiment, such that they approach angular peaks and valleys, as compared with the relatively cur bends 15p, 15v of the first embodiment (see FIG. 3). The embodiment of FIG. 4 affords a stiffer stent in the expanded state than that of FIG. 3. However, at the same time, the embodiment of FIG. 3 opens more evenly, leaving fewer irregularities and gaps in the expanded stent than does the embodiment of FIG. 4.

Figure 5A:
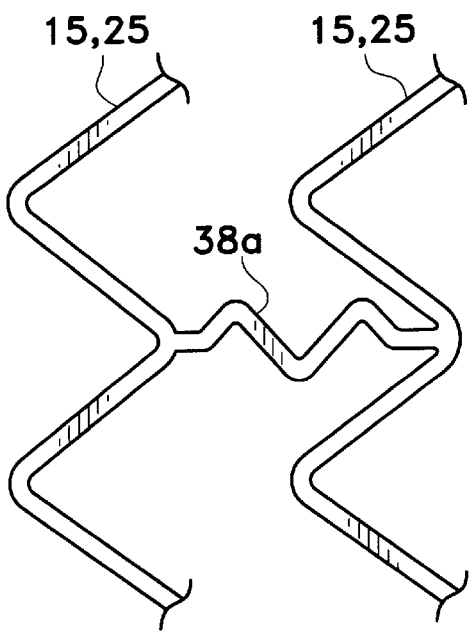
FIG. 5a is a partial view of a stent embodying a variation of a bridge to interconnect adjacent undulations.
Figure 5B:
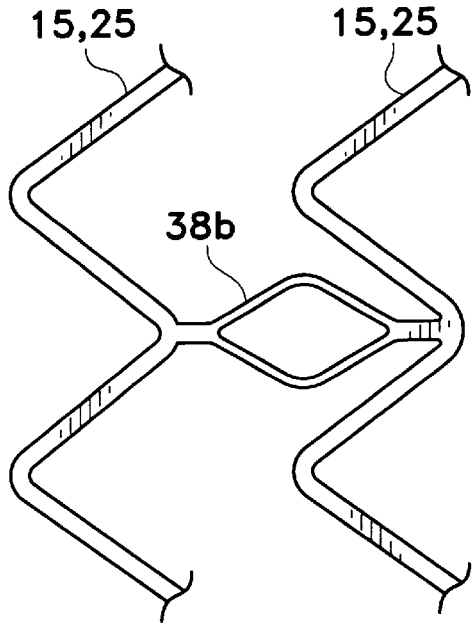
FIG. 5b is a partial view of a stent embodying a second variation of a bridge to interconnect adjacent undulations.
Figure 5C:
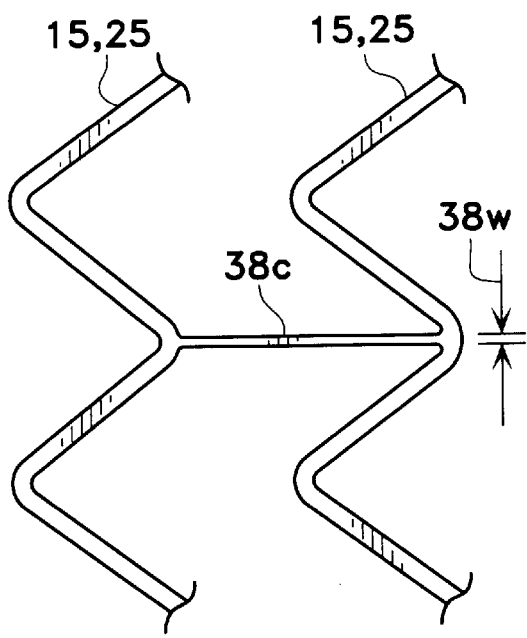
FIG. 5c is a partial view of a stent embodying a third variation of a bridge to interconnect adjacent undulations.

To provide additional control in the design of the flexibility of the stent, the construction of the bridges may be modified from the straight strut-type design 18, as shown by three examples 38a, 38b and 38c in FIGS. 5a, 5b and 5c, respectively. It is noted that although the members 38a, 38b and 38c are shown in combination with the undulation members of the first and second embodiments of the present invention, the modified bridges may be applied generally to any of the embodiments disclosed herein, and to the invention in general.

In FIG. 5a, the bridge has been modified to form an undulating, spring type member 38a which affords more compressibility in the direction aligned with the longitudinal axis of the cylindrical stent. The bridge 38a also increases the bendability (i.e., reduces the bending strength) in radial directions. It is further noted that a stent could be specifically tailored for asymmetrical bending and strength characteristics by individually designing only predetermined bridges 18 as spring type bridges 38a. Thus, as few as zero or one of the bridges 18 could be formed as a spring bridge 38a, or as many as all of the bridges in a stent could be so formed. Generally, it is preferred that all of bridges 18, or a symmetrical configuration of a portion of bridges 18 are formed as spring bridges 38a, so as to give symmetrical bending and strength characteristics. However, this is not always the case and the invention is not to be so limited.

FIG. 5b, shows a bridge which has been modified to form leaf-spring like member 38b, which also affords more compressibility in the direction aligned with the longitudinal axis of the cylindrical stent. Likewise, bridge 38b also increases the bendability (i.e., reduces the bending strength) in radial directions. Similar to spring bridge 38a, a stent could also be specifically tailored for asymmetrical bending and strength characteristics by individually designing only predetermined bridges 18 as spring type bridges 38b. Thus, as few as zero or one of the bridges 18 could be formed as a spring bridge 38b, or as many as all of the bridges in a stent could be so formed. Generally, it is preferred that all of bridges 18, or a symmetrical configuration of a portion of bridges 18 are formed as spring bridges 38b, so as to give symmetrical bending and strength characteristics. However, this is not always the case and the invention is not to be so limited.

By making the stent more compressible with the aforementioned spring type designs, the folding or compression profiles of the resultant stents may be negatively effected. FIG. 5c shows a third alternative way to increase compressibility and flexibility without negatively effecting the folding or compression profile of the resultant stent. In this embodiment, one or more of the bridges is made more compressible and bendable by reducing the width 38w of bridge 38c. Thus, width 38w of bridge 38c is less than the width of undulating member 15,25, etc. Not only does this configuration not negatively effect the compression or folding profile of the resultant stent, it may actually positively effect such profiles, and also reduces the overall weight of the resultant stent. As with the embodiments of FIGS. 5a and 5b, as few as zero or one of bridges 18 could be formed as a narrow bridge 38c, or as many as all of the bridges in a stent could be so formed. Generally, it is preferred that all of bridges 18, or a symmetrical configuration of a portion of bridges 18 are formed as narrow bridges 38c, so as to give symmetrical bending and strength characteristics. However, this is not always the case and the invention is not to be so limited.

Figure 5D:
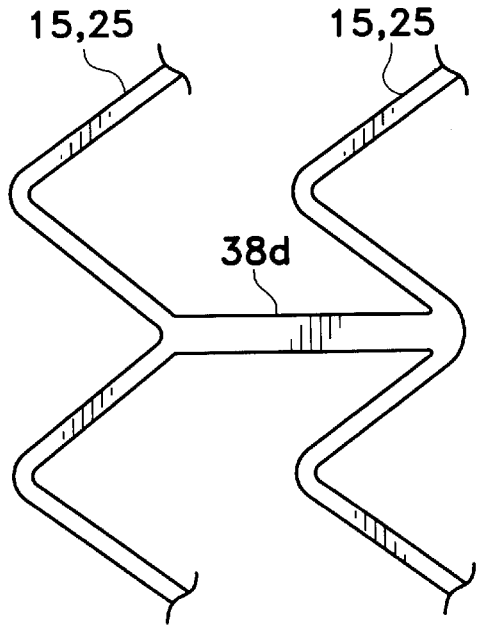
FIG. 5d is a partial view of a stent embodying a fourth variation of a bridge to interconnect adjacent undulations.

It is further noted that the embodiment of FIG. 5d could also be employed to increase the strength of the resultant stent when in the expanded position. This would be accomplished by increasing the width of one or more bridges 18 to form wide bridges 38d. Although this is generally not the preferred embodiment of the present invention, it is an option which is available to the stent designer. Of course, the entire structure of the stent, including the undulating member and the bridges may be widened as another option for increasing the strength of the stent. The width ratio of the bridges to undulating members ranges generally from about 0.5:1 up to about 1.5:1, with preferred ratios being about 1:1 or less.

Figure 6:
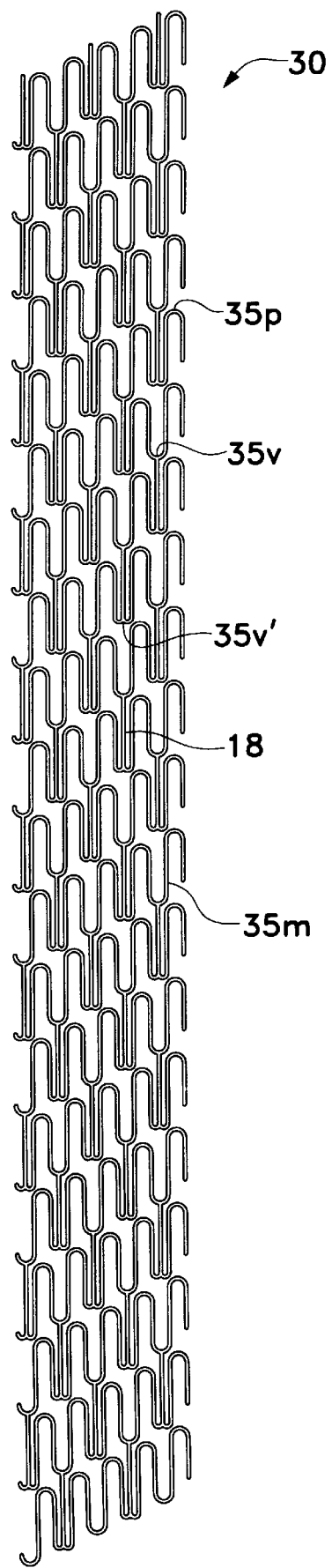
FIG. 6 is a plan view of a flattened section of a stent according to a third embodiment.

FIG. 6 shows a third embodiment of the inventive stent, which includes a pattern that is preferably cut into a smaller diameter tubing, and then expanded to a larger functional diameter and heat set at the larger diameter to give it self-expanding properties. For example, the pattern of the embodiment shown in FIG. 6 could be cut into a nitinol tube having about a 2.0 mm diameter, expanded to about a 4.0 mm diameter and then heat set.

In this embodiment, prior to expansion, it is noted that bends 35p,35v are substantially rounded so as to effectively form semicircles. The members 35m interconnecting the bends 35p, 35v are substantially aligned with the longitudinal axis of the cylindrical tubing from which the stent is cut. Upon expansion, however, the members 35m become substantially transverse to the longitudinal axis of the cylindrical shape of the stent, as will be discussed and shown below with regard to the following embodiment.

Another variation from the previous embodiments, is that although bridges 18 are preferably interconnected between adjacent bends 15p, 15v of the undulating helical turns in order to prevent shortening of the stent during the expansion thereof, the particular bends to which bridges 18 are connected are slightly modified from the unconnected bends 15v, such that the connected valleys 15v' form two substantial semicircles with the bridge 18, one on each side of bridge 18. This variation allows a more even expansion of members 35m out from valley 35v' with respect to bridge 18 upon expansion of the cylinder.

It is to be noted that in this and all other embodiments, the bend elements 15p and 15v are subject to a particular orientation of the stent as shown in the Figures. Accordingly, the elements 15p and 15v can be interchanged with regard to any of the embodiments described herein, as long as they are interchanged consistently throughout the entire description of the embodiment. Such an interchange would be tantamount to inverting the particular figure(s) referred to by the detailed description of that embodiment.

The helical nature of the stent designs according to the present invention dictates some anomalies in the resultant cylindrical structure of the final product, which may be addressed by the following further embodiments.

Figure 7:
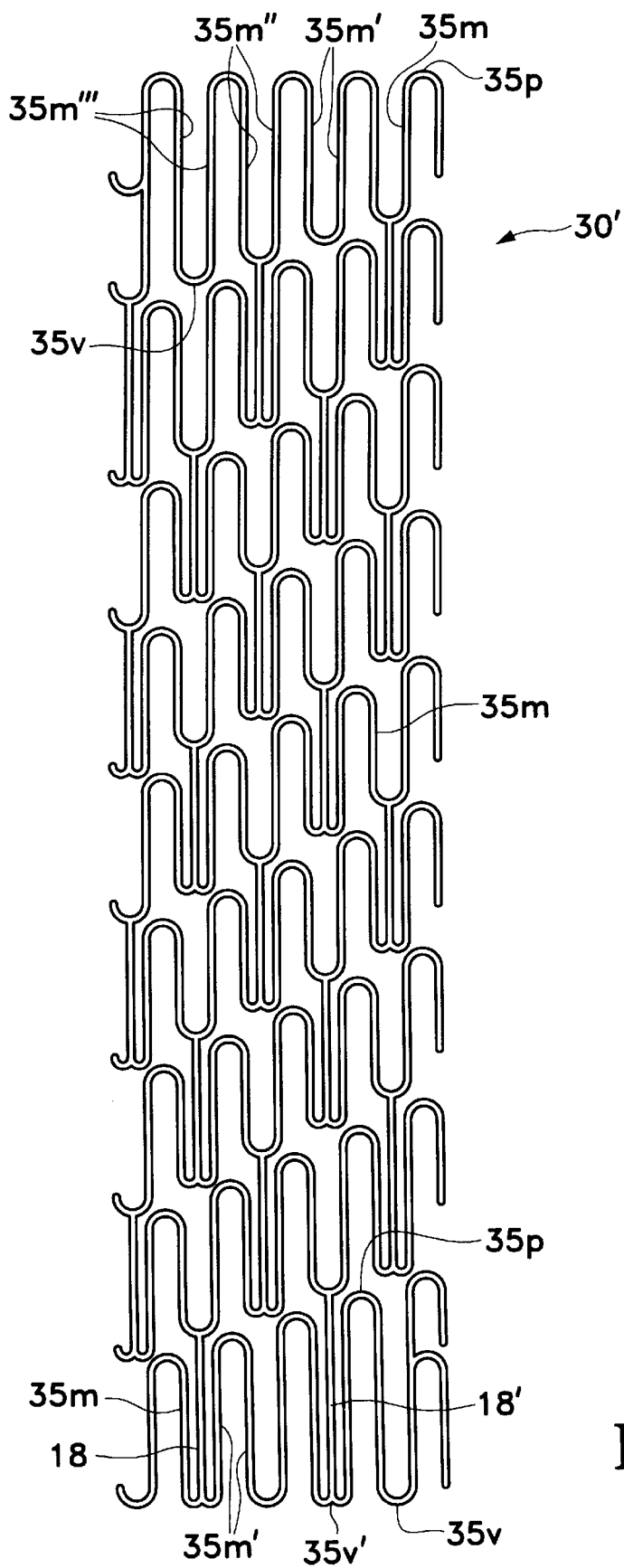
FIG. 7 is a plan view of a flattened section of a stent according to a variation of the third embodiment shown in FIG. 6.

FIG. 7 shows a modification of the embodiment of FIG. 6 in which the end portions of the cylinder that form the stent have been modified, so that both ends form "square ends" i.e., circles which are substantially perpendicular to the longitudinal axis of the cylindrical shape of stent 30'. In order to effectuate such "square ends", the lengths of the members connecting the bends 35p,35v(35v') are gradually increased to compensate for the pitch angle of the helix (e.g., see the progression of lengths: 35m, 35m', 35m", . . . ). Additionally, any bridges which interconnect bends 35p,35v, which are also connected by lengthened members (35m', 35m" etc.) also must follow a progressive lengthening scheme (e.g., see 18, 18', . . . )

Figure 8:
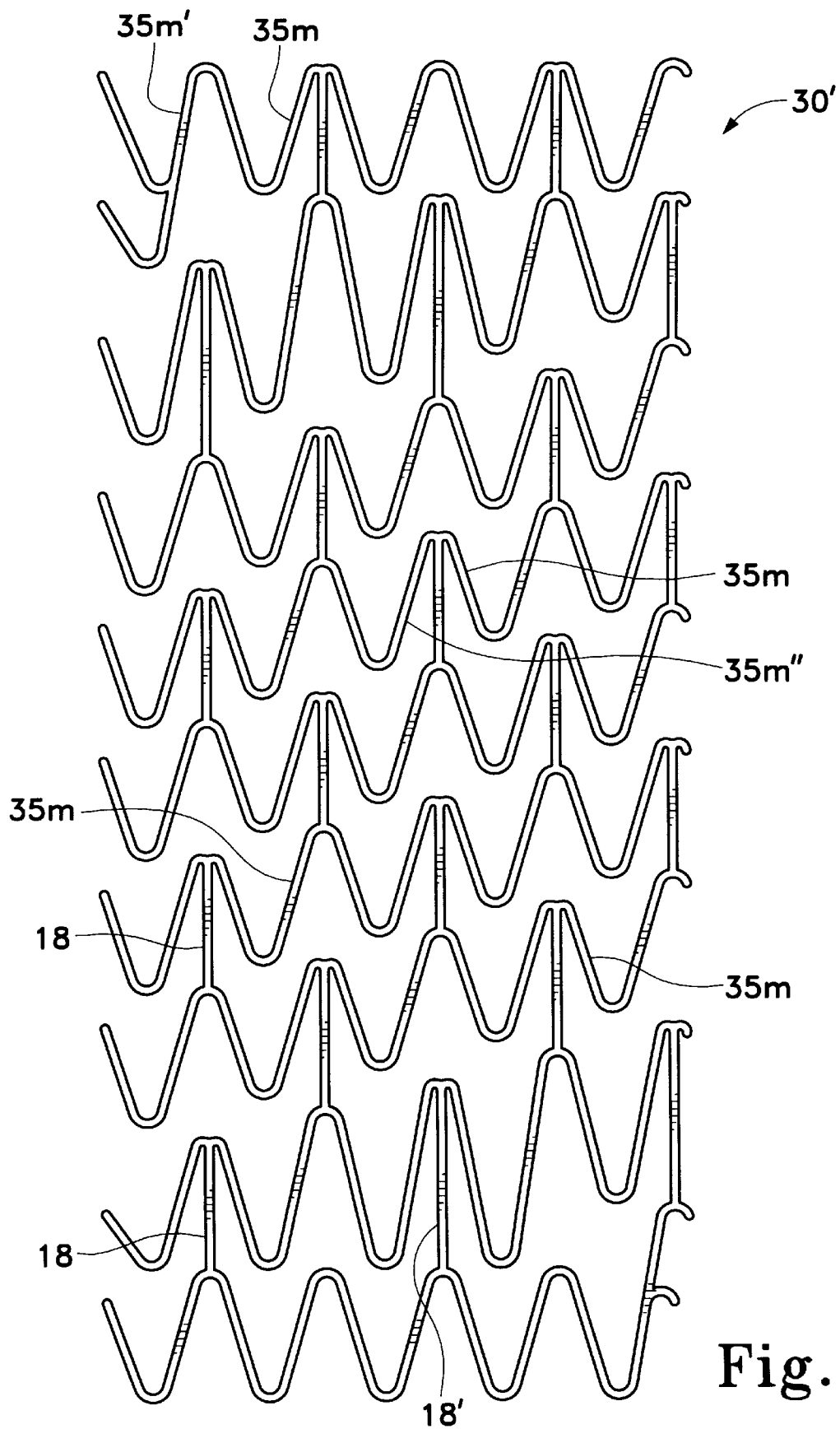
FIG. 8 is a plan view of the stent shown in FIG. 7 after expansion of the same.

FIG. 8 shows stent 30' in the expanded state at which it is to be heat set. As noted with regard to the similar embodiment in FIG. 6, prior to expansion, the bends 35p,35v are substantially rounded so as to effectively form semicircles (see FIG. 7), and the members 35m, 35m', 35m", . . . interconnecting the bends 35p and 35v,35v' are substantially aligned with the longitudinal axis of the cylindrical tubing from which stent 30' is cut. Upon expansion, however, members 35m, 35m' . . . become substantially transverse to the longitudinal axis of the cylindrical shape of stent 30', while bridges 18, 18' . . . maintain a substantially parallel positioning to the longitudinal axis. Thus, the bridges maintain their maximum potential for longitudinally strengthening stent 30'.

Figure 9:
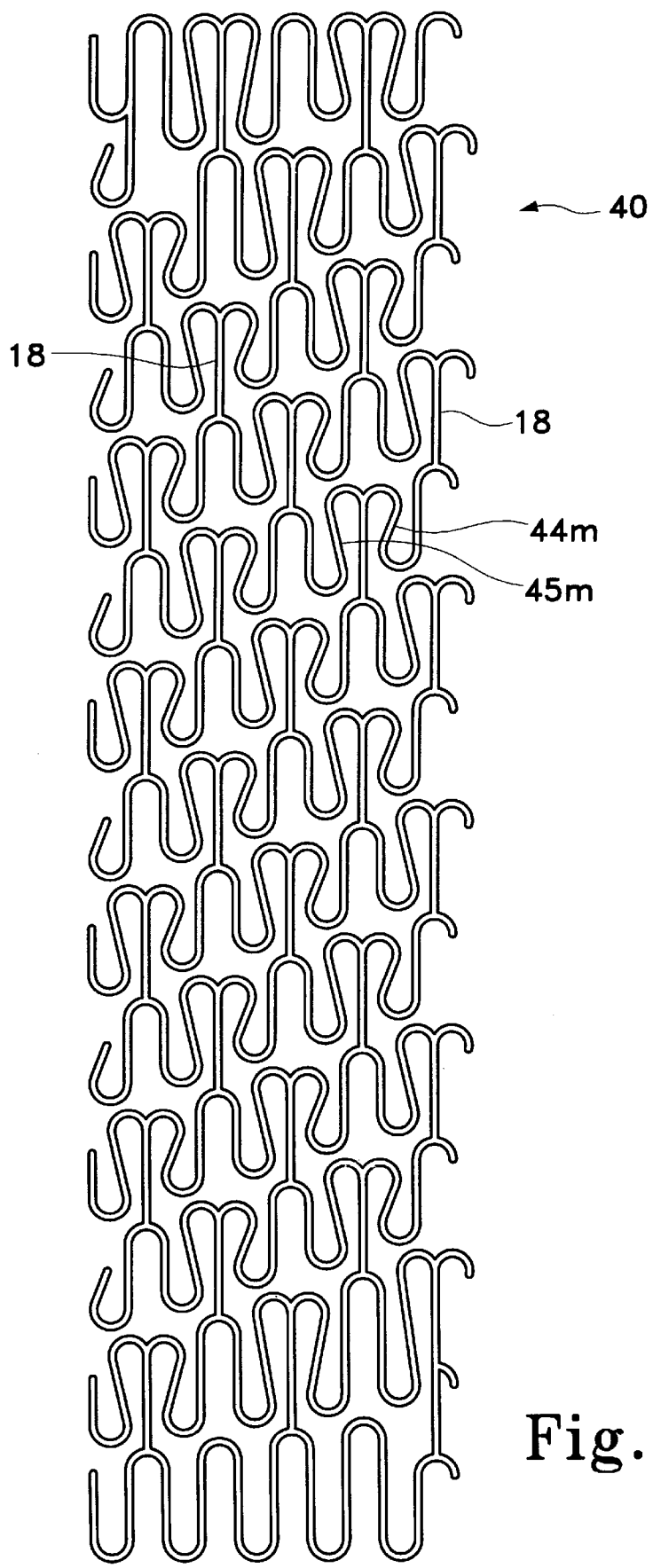
FIG. 9 is a plan view of a flattened section of a stent according to a fourth embodiment of the present invention.

Another anomaly dictated by the helical nature of the stent structures described above, is that some members 35m" throughout the stent necessarily have somewhat longer lengths compared to the standard length member 35m. This is due to the nature of the helical windings which progressively move away from the previous adjacent helical winding, and thus require some longer members to compensate for the pitch angle of the helix and maintain a standard bridge length. Because not all of the member lengths are equal, upon expansion of the stent, some uneven or unequal gaps between bridges 18 and members, e.g., 35m, 35m" also occur. In order to compensate for these abnormalities in spacing, stent 40 shown in FIG. 9, includes asymmetrical members 44m and 45m which connect to one end of each bridge on opposite sides thereof. Because member 44m has a greater degree of curvature than member 45m, it allows for a greater degree of expansion on the side of member 44m, which compensates for the unevenness in expansion caused by the helical windings.

Figure 10:
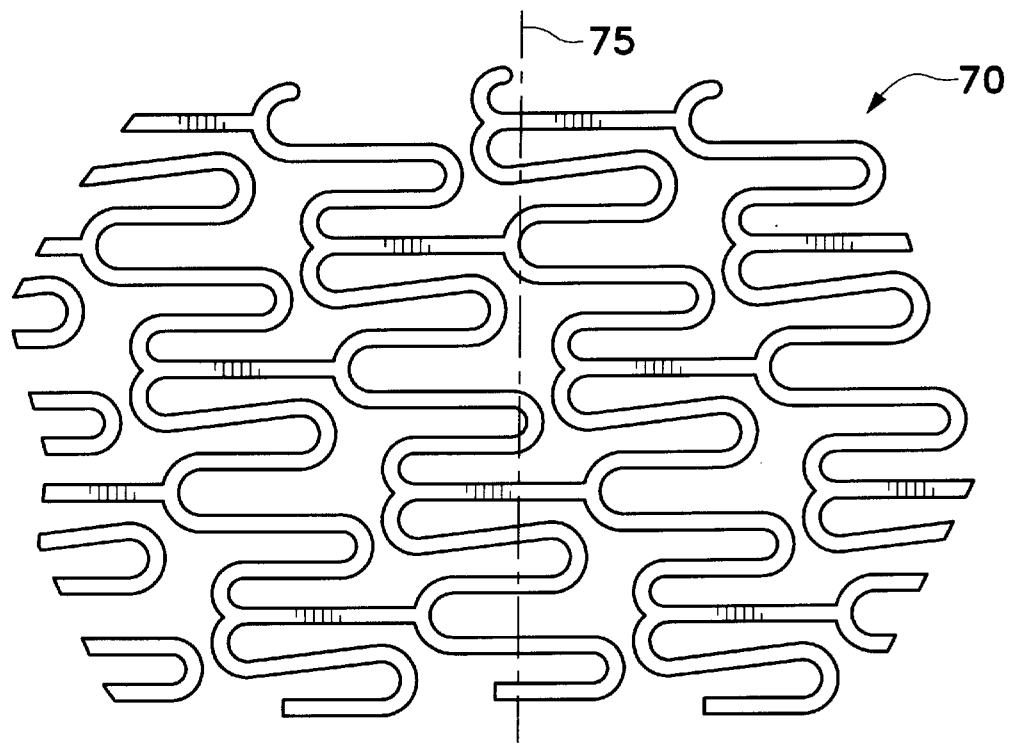
FIG. 10 is a partial flattened section of a stent according to an embodiment similar to that shown in FIG. 9.
Figure 11:
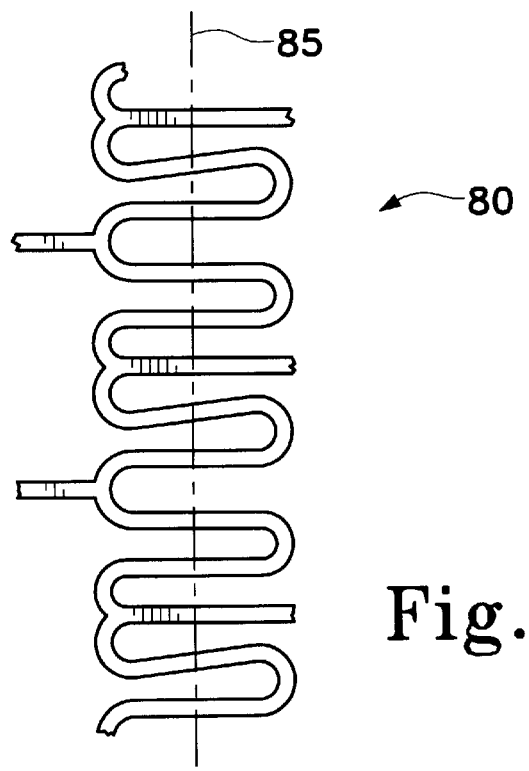
FIG. 11 is a partial flattened section of a stent formed with the same undulating pattern as the stent shown in FIG. 10, but in a ring configuration as opposed to a helical configuration, for comparison purposes.

As mentioned above, it is believed that the helical stent according to the present invention can be compressed to a smaller delivery profile than can a stent formed of individual rings, or other ring type structure. FIG. 10 shows a flattened section 70 of a helical stent like the embodiment shown in FIG. 9, wherein the stent has been cut longitudinally parallel to the longitudinal axis and flattened out into a substantially planar structure. FIG. 11 shows a flattened section 80 of a stent formed with the same undulating pattern as the stent shown in FIG. 10, but in a ring configuration as opposed to a helical configuration, for comparison purposes.

Imaginary lines 75 and 85 are drawn perpendicular to the longitudinal axes of the stent portions 70 and 80, respectively. The total number of structures (including bridges and members) which are intersected by the line 75 is 11 as compared to 13 structures which are intersected by line 85. The difference is explained by the helical structure of FIG. 10, which more continuously distributes the mass of the structure along the entire length of the stent. On the other hand, the mass of the ring type stent shown in FIG. 11 is more concentrated in the rings, with a lower concentration in the areas connecting between the rings. The minimum profile to which a stent can be reduced is limited by that portion of the stent which has the largest diameter after reduction of the stent for delivery. Thus, the profile of the ring type stent is expected to be larger than the helical stent since the largest sections of the ring type stent include 13 structures within the radius thereof, as compared to 11 within the radii of the sections throughout the helical stent.

Figure 12A:
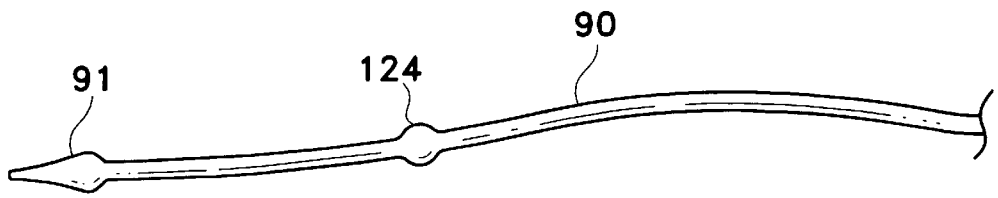
FIGS. 12a, 12b and 12c are views of preferred apparatuses for preparing for deployment and deploying a stent according to the present invention.
Figure 12B:
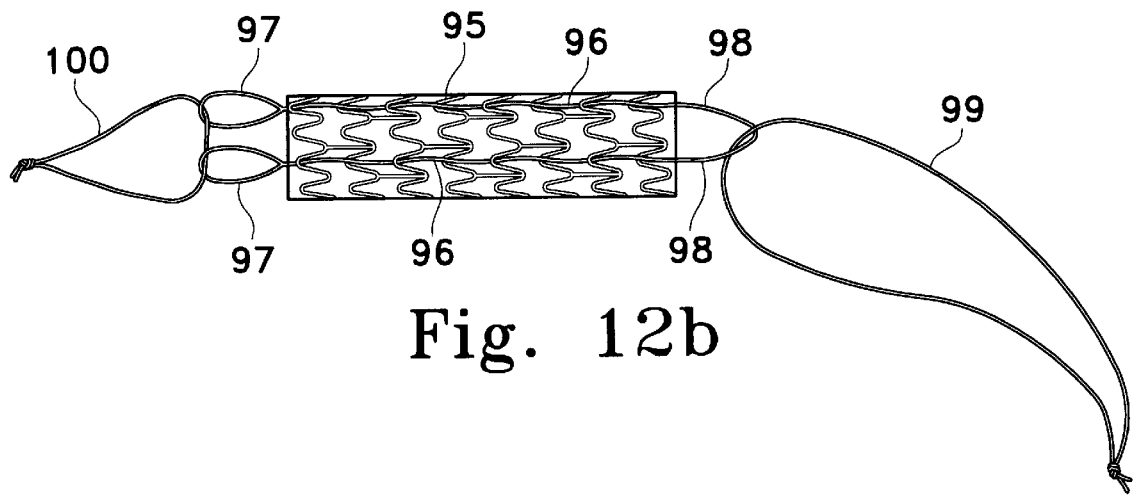
Figure 12C:
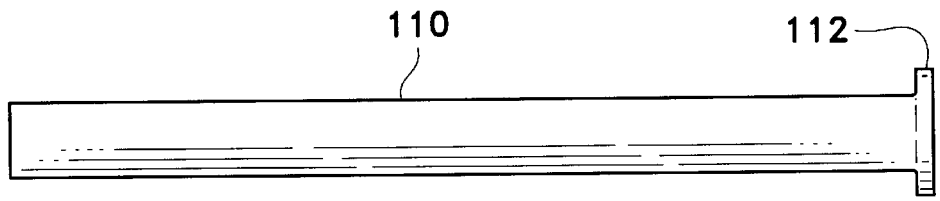

FIGS. 12a–12c show various equipment used in the preferred method for preparing a stent according to the present invention for deployment as well as for deploying the stent. Preferably, a self-expanding stent is radially crushed or compressed to have a reduced diameter for introduction into a vessel into which it is to be implanted. Alternatively, the stent may be folded and held in the folded state during the introduction phase, or a stent may be formed in a smaller diameter, introduced into the vessel and then expanded by a balloon catheter or the like.

Preferably, a self-expandable stent is compressed by drawing the same through a funnel, to be discussed in detail below. The stent is held in the compressed state within a sleeve. Within the sleeve is placed a catheter 90, as shown in FIG. 12a. Catheter 90 functions to guide the stent and the entire apparatus through the vessel and to the implant site. Catheter 90 includes an enlarged diameter portion 124 which has an outside diameter larger than the inside diameter of the stent in its compressed state. Thus, enlarged diameter portion 124 functions to prevent the compressed stent 95 from sliding in a direction toward the proximal end of the catheter 90. The distal end of catheter 90 is adapted to receive "olive" 91. The outside diameter of olive 91 is larger than the inside diameter of the stent in its compressed state. Thus, affixation of olive 91 to the distal end of catheter 90, functions to prevent any tendency of the compressed stent to slide off the distal end of catheter 90 prior to implantation of the stent. Catheter 90 is preferably made of polyimide, but other known equivalent materials suitable for such purpose, may be substituted.

In order to apply sufficient pulling force to draw stent 95 through a funnel for compression thereof, filaments 96 are preferably woven through the members of stent 95 and formed into loops 97 and 98 extending from opposite end of stent 95, as shown in FIG. 12b. Filaments 96 are preferably commercially available sutures and preferably are CV-7 GORETEX sutures (manufactured by W. L. Gore). Of course, other gauges of suturing materials may be substituted, and other materials may be used as well, e.g., stainless steel wire, various polymeric filaments, etc. Filaments which are preferably thicker than filaments 96 are next looped through loops 97 and 98 to form a short pulling line 100 and a long pulling line 99, respectively. Pulling lines 99 and 100 are preferably formed from 5.5 gauge suturing materials, but other substitutes may be used, similar to the substitutes for filaments 96.

Sleeve 110 (FIG. 12c), like catheter 90, is preferably made of polyimide, but other known equivalent materials for such purpose may be substituted. The inside diameter of sleeve 110 is designed to be substantially equal to, or slightly larger than the intended outside diameter of stent 95 when in the compressed state. The proximal end of sleeve 111 flares out to an enlarged control handle 112 which can be grasped for retraction of the sleeve during deployment of stent 95.

After interweaving filaments 96 with stent 95 and connecting pulling lines 99 and 100, the preparation for deployment of stent 95 continues by axially aligning funnel 130 with sleeve 110, as shown in FIG. 13a. Funnel 130 is preferably formed of stainless steel, however, other relatively rigid materials which exhibit a low friction characteristic with regard to the stent materials may be used. For example, high density thermoplastics or thermosetting polymers could be used, with or without a low friction inner coating material applied thereto. Other metals such as titanium, tantalum, silver and gold may also be used. Any other materials known to be sufficiently nonimmunogenic, and which would exhibit sufficient strength to compress the stents according to the present invention, while also exhibiting a low friction characteristic with regard to the present stent materials, may be used.

Funnel 130 has a distal inside diameter 131 that is slightly larger than the outside diameter of stent 95 when in the uncompressed state. The inside diameter of funnel 130 gradually tapers from distal inside diameter 131 to a proximal inside diameter 132 which is slightly less than the inside diameter of sleeve 110, so that when stent 95 is pulled through funnel 130, the resultant compressed stent 95 slides easily into sleeve 110 which then maintains stent 95 in the compressed state.

Upon axial alignment of funnel 130 with sleeve 110, long pulling line 99 is then threaded through funnel 130 and sleeve 110 to protrude from the proximal end of sleeve 110 as shown in FIG. 13a. Stent 95 is then axially aligned with funnel 130 and maintained in this position by applying a slight pulling force via pulling line 99. Short pulling line 100 may be used to assist in manipulation of stent 95 to ensure proper axial alignment thereof. By gradually and steadily increasing the pulling force on pulling line 99, stent 95 begins to be compressed as it is pulled along the continuously decreasing inner diametrical surface of funnel 130.

As the stent is pulled through the proximal end (i.e., proximal inside diameter) of funnel 130 it has attained an outside diameter which is slightly smaller than that of its final compressed state, and thus slides relatively easily into sleeve 110. Once the stent has been pulled completely into sleeve 110, as shown in phantom in FIG. 13b, the pulling force is discontinued. Stent 95, upon entering sleeve 110, expands slightly to abut the inner circumference of sleeve 110 and assume the final compressed diameter. Withdrawal of filaments 96 from stent 95 can be accomplished in at least two different manners. Short pulling line 100 may be cut and withdrawn from engagement with loops 97. Afterwards, pulling line 99 is withdrawn from sleeve 110, drawing filaments 96 out along with it. Alternatively, pulling line 99 may be cut and withdrawn from engagement with loops 98. Afterward, pulling line 100 is withdrawn from funnel 130, drawing filaments 96 out along with it.

After removal of the pulling lines 99,100 and filaments 96, funnel 130 is removed, leaving stent 95 compressed within sleeve 110. Next, the proximal end of catheter 90 is inserted through the tubular opening of compressed stent 95 and sleeve 110 as shown in FIG. 13c. Catheter 90 is slid entirely through sleeve 110 until enlarged diameter portion 124 abuts against compressed stent 95 and the distal end of catheter 90 becomes substantially aligned with the distal end of sleeve 110.

Figure 13D:
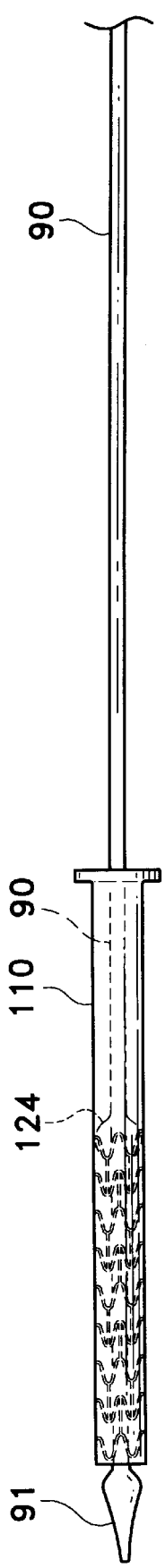

Olive 91 is next fixably attached to the distal end of catheter 90, as shown in FIG. 13d, to abut against the distal end of sleeve 110 so as to prevent movement of compressed stent 95 in the distal direction. Olive 91 is preferably adhesively bonded to catheter 90 using any of a variety of well-known, biocompatible adhesives which would be readily known and available to those of ordinary skill in the art. Alternatively, olive 91 could be screw threaded, heat bonded, spin welded, or fixed to catheter 90 by a variety of other known techniques which would be equivalent for purposes of this invention. At this stage, the apparatus is fully assembled for insertion into a vascular site or bodily organ, for deployment of stent 95.

After the apparatus has been inserted to the desired implantation site, the operator grasps both control handle 112 and catheter 90 to begin the deployment of stent 95. The operator maintains the position of catheter 90 while steadily and slowly withdrawing control handle 112 away from the site of implantation. As a result, enlarged diameter portion 124 maintains the stent 95 in the desired location by its abutment with the proximal end of stent 95, as sleeve 110 is slid with respect to stent 95 and gradually withdrawn from engagement therewith. Thus, stent 95 remains in the desired implantation site and is prevented from being dragged along with the sleeve 110 by enlarged diameter portion 124, upon withdrawal of sleeve 110 from the implantation site.

Figure 13E:
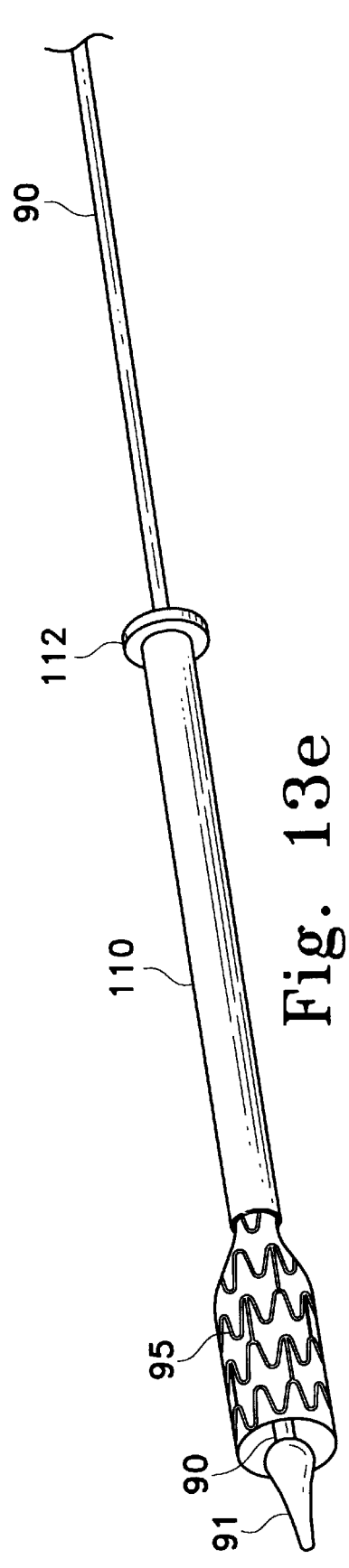
Figure 13F:
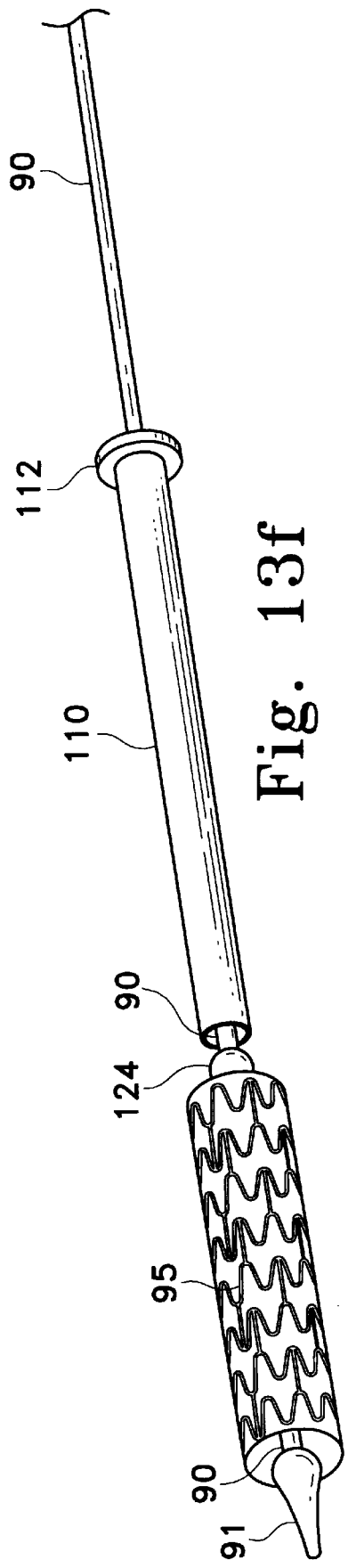

FIG. 13e shows that stent 95 self expands as sleeve 110 is withdrawn from contact therewith. Upon complete removal of contact between sleeve 110 and stent 95, the stent resumes its previous uncompressed configuration as shown in FIG. 13f, thereby abutting the walls of the vessel into which it has been implanted. The operator then begins to withdraw catheter 90, until catheter 90 and olive 91 are completely withdrawn from the organism into which the implantation is performed, to allow follow-up closure procedures to be carried out.

Figure 14A:
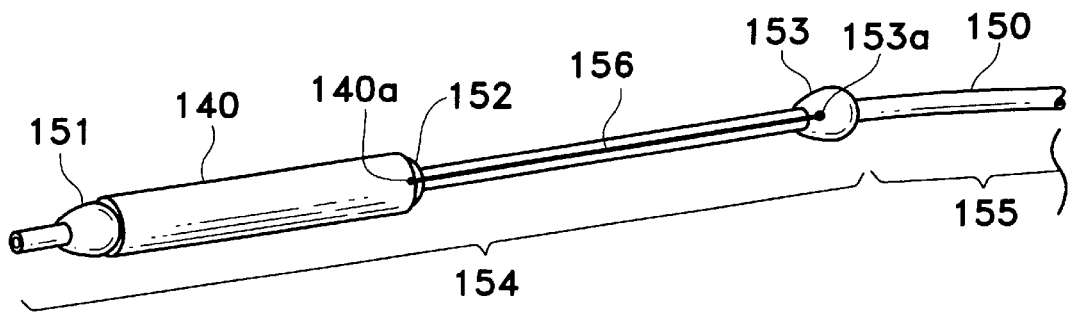
FIGS. 14a, 14b and 14c show another arrangement for deploying a stent according to the present invention, at various stages of deployment.
Figure 14B:
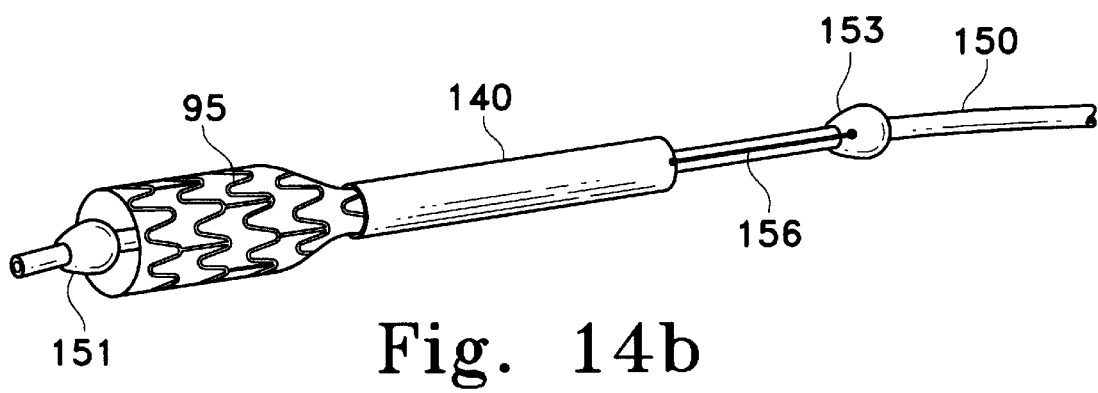
Figure 14C:
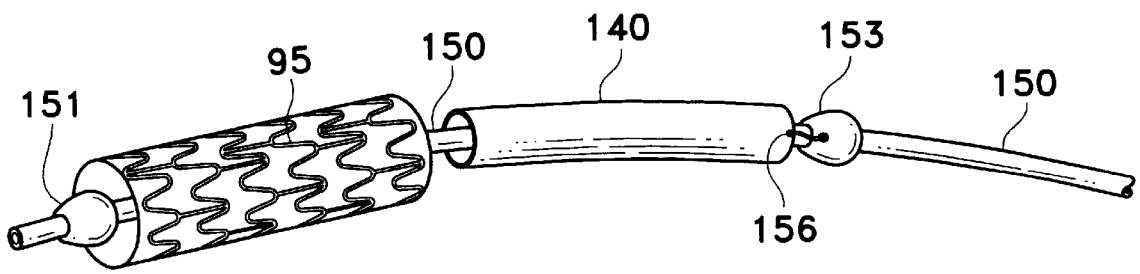

FIGS. 14a–14c show an alternative arrangement used in preparation for deployment, and deployment of, a stent according to the present invention. In this embodiment sleeve 140 is not designed to extend from the implantation site all the way out of the organism for direct manipulation by the operator, as in the case of the embodiment discussed above. Rather, sleeve 140 is only slightly longer than stent 95 to ensure that stent 95 can be completely and reliably maintained therewithin in the compressed state. Sleeve 140 is preferably formed of polyimide, but substitute materials are applicable, just as discussed with regard to sleeve 110.

Catheter 150 is provided with both a distal olive 151 and a proximal olive 152 for maintaining the compressed stent in position prior to deployment. Stent 95 is compressed within sleeve 140, in much the same manner as described above with regard to sleeve 10. Catheter 150 is then inserted in much the same manner as described above with regard to catheter 90, and olive 151 is then connected in much the same manner as described above with regard to olive 91.

Catheter 150 further includes proximal transition 153 for transitioning the catheter from the distal portion of the catheter 154, which carries the sleeve 140 and the graft 95, and the proximal portion of the catheter 155, which is the rest of the catheter that is proximal to the proximal transition 153. A tether line or draw cord 156 is fixed to the proximal end 140a of sleeve 140. The tether line or draw cord (hereafter, tether line) 156 may be formed from stainless steel wire, high strength and biocompatible polymer fibers, or the like equivalents known in the art. Tether line 156 also is slidably fixed to proximal transition 153 at 153a, where tether line 156 passes internally of the proximal portion 155 of the small diameter catheter. Tether line 156 extends out the proximal end of the small diameter catheter 150 (not shown) for manipulation by the operator.

As shown in FIG. 14b, deployment of stent 95 begins when the operator has successfully located the distal end of the small diameter catheter 150, and thus stent 95, in the desired location. The operator then begins to steadily and gradually pull tether line 156, so as to retract sleeve 140 from its position around stent 95. Consequently, graft 95 begins to self-expand in a continuous manner as portions of the stent 95 are continuously freed. Olive 152 prevents the compressed proximal end of stent 95 from sliding with respect to the small diameter catheter 150, and thus prevents retraction of stent 95 along with sleeve 140.

Upon complete retraction of sleeve 140 and expansion of graft 95, the deployment apparatus, including small diameter catheter 150, sleeve 140 and tether line 156 can be withdrawn from the organism as a unit, for follow-up closing procedures.

Although the embodiments of the present invention have been described herein with reference to the accompanying drawings and the particular structures depicted therein, obviously many modifications and changes may be made by those of ordinary skill in the art without departing from the scope of the invention as defined by the claims which follow.

What is claimed is:

1. A stent comprising:
    a structure having a helically configured undulating member containing multiple undulations each with an apex, said member disposed around a longitudinal axis to define a generally tubular shape having multiple turns around said axis with first and second ends; and substantially longitudinally extending bridge members interconnecting at least one apex of one helical turn to at least one apex of an adjacent helical turn, wherein said interconnected apexes extend toward said first end.

2. The stent of claim 1, wherein said bridge members each interconnect an undulation of one turn which is in-phase with an undulation of an adjacent turn.

3. The stent of claim 1, wherein said bridge members are aligned in a direction substantially parallel to said longitudinal axis.

4. The stent of claim 1, wherein said stent lacks any anchoring projections when said stent is in an expanded configuration.

5. The stent of claim 1, wherein said bridges are helically arranged in said structure.

6. The stent of claim 1, wherein said helical structure is formed from a thin-walled tubing.

7. The stent of claim 6, wherein said helical structure is laser cut from said thin-walled tubing.

8. The stent of claim 6, wherein said helical structure is cut from said thin-walled tubing.

9. The stent of claim 6, wherein said helical structure is cut from said thin-walled tubing by EDM programming.

10. The stent of claim 1, wherein said bridges are circumferentially and substantially equiangularly located about said helix, with respect to adjacent ones of said bridges.

11. The stent of claim 9, wherein said bridge members are positioned to form a ratio of about 2 to 4 bridge members per 360° of said helical member.

12. The stent of claim 11, wherein said bridge members are positioned to form a ratio of about 3 bridge members per 360° of said helical member.

13. The stent of claim 1, wherein at least one of said bridge members comprises a straight strut.

14. The stent of claim 1, wherein at least one of said bridge members comprises a spring having a predetermined spring constant.

15. The stent of claim 14, wherein said spring comprises an undulating spring.

16. The stent of claim 14, wherein said spring comprises a leaf-spring.

17. The stent of claim 14, wherein said at least one of said bridge members comprises a spring aligned in a direction substantially parallel to said longitudinal axis generally tubular shape.

18. The stent of claim 1, wherein said helical member and said bridge members have substantially equal thicknesses.

19. The stent of claim 1, wherein said helical structure and said bridge members have substantially equal widths.

20. The stent of claim 1, wherein at least one of said bridge members comprises a width which is substantially less than a width of said helical member.

21. The stent of claim 1, wherein said stent comprises a self-expandable stent capable of being compressed for delivery, and being self-expandable when removed from a compressive force.

22. The stent of claim 1, wherein said stent is expandable by application of force via a balloon catheter.

* * * * *